United States Patent [19]
Berman

[11] Patent Number: 6,146,418
[45] Date of Patent: *Nov. 14, 2000

[54] BODY IMPLANT AND METHOD OF IMPLANTING

[76] Inventor: Mark Berman, 1551 Ocean Ave., #200, Santa Monica, Calif. 90401

[*] Notice: This patent issued on a continued prosecution application filed under 37 CFR 1.53(d), and is subject to the twenty year patent term provisions of 35 U.S.C. 154(a)(2).

[21] Appl. No.: 09/162,477

[22] Filed: Sep. 28, 1998

Related U.S. Application Data

[63] Continuation-in-part of application No. 08/807,706, Feb. 28, 1997, abandoned.

[51] Int. Cl.[7] .................................................. A61F 2/12
[52] U.S. Cl. ............................................. 623/8; 623/7
[58] Field of Search ....................................... 623/7, 8

[56] References Cited

U.S. PATENT DOCUMENTS

| | | | |
|---|---|---|---|
| 4,433,440 | 2/1984 | Cohen | 623/8 |
| 4,769,036 | 9/1988 | Modir | 623/8 |
| 4,773,909 | 9/1988 | Chaglassian | 623/8 |
| 4,795,464 | 1/1989 | Eberl et al. | 623/8 |
| 4,820,303 | 4/1989 | Brauman | 623/8 |
| 4,936,858 | 6/1990 | O'Keefe | 623/8 |
| 4,955,907 | 9/1990 | Ledergerber | 623/8 |
| 4,969,899 | 11/1990 | Cox | 623/8 |
| 5,147,398 | 9/1992 | Lynn et al. | 623/8 |
| 5,246,454 | 9/1993 | Peterson | 623/8 |
| 5,376,117 | 12/1994 | Pinchuk et al. | 623/8 |
| 5,496,370 | 3/1996 | Hamas | 623/8 |
| 5,759,204 | 6/1998 | Seare, Jr. | 623/8 |

OTHER PUBLICATIONS

Dow Corning Wright, Data Sheet #L080–0011 Jan. 1983.

*Primary Examiner*—Paul J. Hirsch
*Attorney, Agent, or Firm*—Gifford, Krass, Groh, Sprinkle, Anderson & Citkowski, P.C.

[57] ABSTRACT

A human body implant has a separate bladder made from a bio-compatible flexible polymer into which a mobile device or prosthesis is placed after the bladder has been introduced into a subcutaneous body pocket. The bladder completely forms an artificial scar by ingrowth of body tissue into pores in the bladder to form an artificial scar. In the case of a breast implant, a breast prosthesis of many different types can be used. The prosthesis is isolated from but is mobile in the bladder. Fluids can be withdrawn from the prosthesis without contaminating the body.

23 Claims, 3 Drawing Sheets

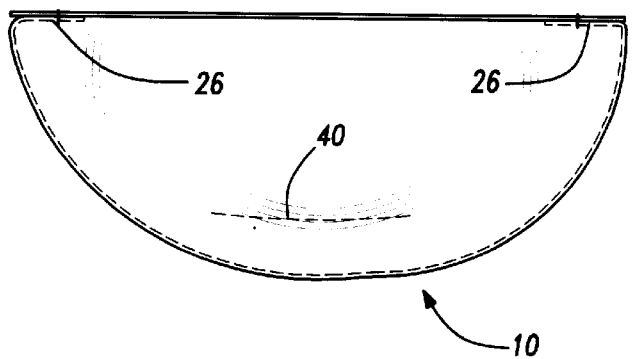
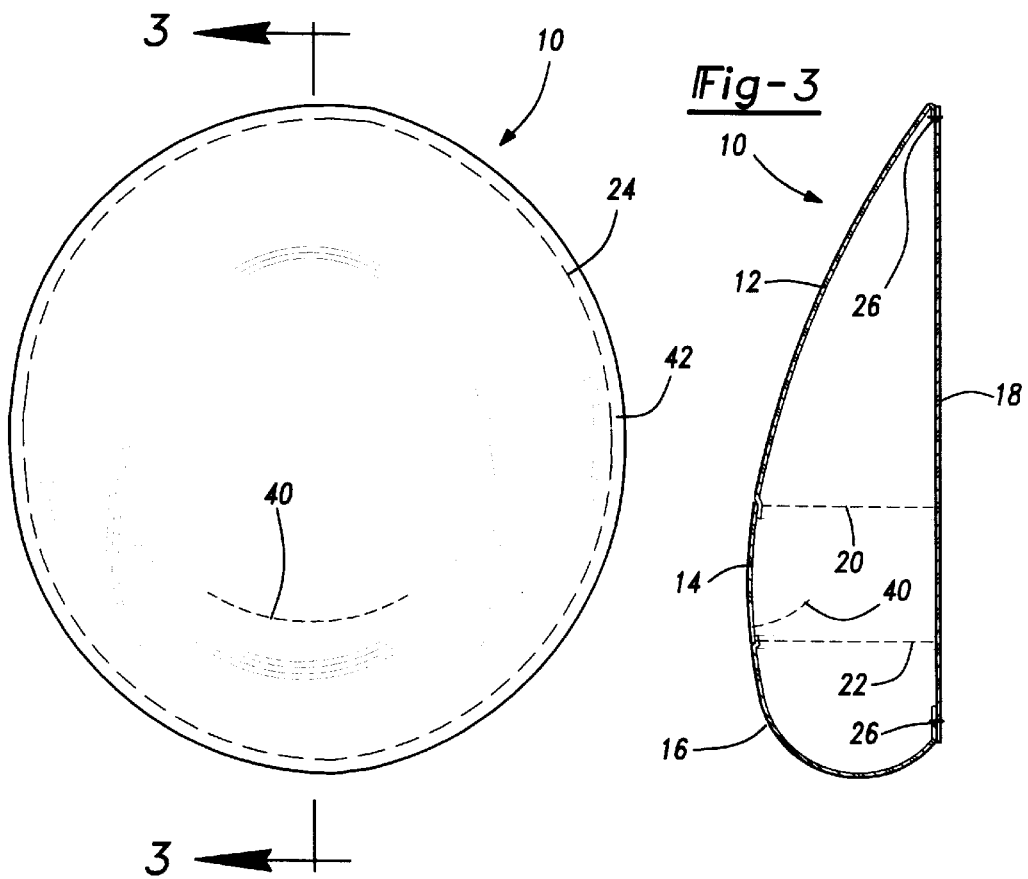

BODY IMPLANT AND METHOD OF IMPLANTING

RELATED APPLICATION

This application is a continuation-in-part of U.S. patent application Ser. No. 08/807,706 filed Feb. 28, 1997 entitled "Body Implant and Method of Implanting" abandoned.

BACKGROUND OF THE INVENTION

I. Field of the Invention

This invention relates to human body implants, and, more particularly, this invention relates to breast prosthesis implants and the method of implanting.

II. State of the Prior Art

In all types of body implants, interfacing the device with the body in the subcutaneous pocket presents the problem that normal tissue reaction to the device as a foreign object causes fibrous scar tissue to build a natural capsule surrounding the device with the scar tissue normally undergoing contraction during the healing process producing spherical capsular contracture or an infection which results in relatively rigid structure producing discomforture or an undesirable shape which in the case of plastic surgery or particularly facial plastic surgery and breast implant can be so aesthetically displeasing as to be totally unsatisfactory. Various approaches have been used to combat the problem such as texturing the outside surface of the device as set forth in U.S. Pat. 4,963,150 in which the outside surface of a conventional silicone rubber implant filled with silicone gel is textured to reduce contracture. Other means have modified the containment sac or envelope to resist the pressure of the contracting scar tissue so as to resist the tendency to misshape the device or prosthesis as shown in U.S. Pat. 4,264,990 and 4,205,401.

SUMMARY OF THE INVENTION

The present invention overcomes the disadvantages of the prior art implants by providing a separate bladder into which a mobile device or prosthesis is placed. The bladder is made from a bio-compatible flexible thermoplastic polymer having at least its outer surface porous so that after implantation in a subcutaneous pocket, body tissue will grow into the pores to form an artificial scar with minimum spherical capsular contracture. The bladder is expandable to a predetermined shape and has an inlet through which the device or prosthesis implant is introduced, the inlet being closed after introduction of the device. The device can range from a medication dispensing device or a physiological regulator such as a pacemaker to various prostheses such as facial tissue, penial and breast implants. The device can be replaced in the bladder without disturbing the artificial scar. Such replacement can be, for example, to renew or change the medication charge, change the size or resiliency of the prosthesis or to accommodate aging or other physical change, and to modify physiological regulation. In the case of breast implants, if the containment sac is ruptured, the liquid will be harmlessly contained within the bladder and can be removed and replaced at will. With the use of silicone gel implants falling under disfavor because of extensive litigation, the use of silicone gel or any other new or replacement can be made safe by its containment of the entire breast prosthesis within the bladder.

When the bladder is to contain a breast prosthesis as the implant it is highly desirable that the implant be not palpable under the breast tissue. This requires a thin bladder material having a thickness of between 0.2 mm and 1.2 mm, preferably between 0.2 and 0.4 mm. The bio-compatible flexible thermoplastic polymer is suitably Teflon® or polytetrafluoroethylene because in its expanded form it is microporous with a pore size and distribution of 15 to 100 microns, with a typical material having an average porosity of 22 microns. This size porosity at least on the external surface of the bladder is desirable for any type of implant to provide the best conditions to allow the body tissue to grow into the pores to form an artificial scar with minimal spherical capsular contracture providing an ideal anchoring of the bladder in the body avoiding skin wrinkling and similar problems. This pore size is also desirable in that it is large enough to encourage body tissue adherence it is small enough to discourage leakage through the bladder. It is also desirable to temporarily anchor the bladder during implantation in some fashion.

The breast prosthesis can take a variety of forms, since the bladder isolates the breast prosthesis from the body. Silicone rubber implants are a good choice since they are available in a variety of sizes and shapes having silicone rubber containment sac filled with silicone gel. There is continuing research on other bio-compatible materials having the tactile properties of silicone gels. Thus there may be a new material developed with perhaps radiolucency and minimum biological effects.

The surgical method of performing the breast prosthesis implant preferably comprises the following steps:

A) making an incision in the patient's breast area, preferably with an areolar incision, and creating a subglandular or submuscular breast pocket by dissection followed by hemostasis;

B) irrigating the breast pocket with antibiotic solution;

C) providing a bio-compatible thermoplastic polymer bladder with at least its outer surface being microporous, the bladder having a wall thickness between 0.2 mm and 1.2 mm and being expandable to a tear drop shape;

D) introducing the bladder into the breast pocket created in step A);

E) securing the bladder in the breast pocket;

F) providing a soft pliable smooth surface breast prosthesis;

G) opening an inlet in the bladder;

H) introducing the breast prosthesis into the bladder through the opened inlet, and expanding the bladder to a desired shape;

I) closing the inlet in the bladder; and

J) allowing host body tissue to grow into pores forming an artificial scar in a manner which prevents or minimizes spherical capsular contracture.

An important result of the present invention is that tissue ingrowth into the bladder is provided without permitting tissue contact with the implant carried by the bladder. To accomplish this result, the bladder is preferably constructed of microporous expanded polytetrafluoroethylene (e-PTFE). The microporous nature of this material insures that the outer surface of the bladder is incorporated by tissue ingrowth while the inner surface of the bladder prevents contact with the body and shields any potential implant from contact with the body.

To insure that the bladder will prevent contact between tissue materials and the implant, a coating of silicone or other non-porous material can be provided on the inner surface of the bladder.

BRIEF DESCRIPTION OF THE DRAWING

The advantages of the present invention will be more apparent from the following detailed description when considered in connection with the accompanying drawing wherein:

FIG. 1 is an end view of a bladder suitable for a breast prosthesis implant;

FIG. 2 is a plan view of the bladder of FIG. 1;

FIG. 3 is a side view of the bladder of FIG. 1;

DETAILED DESCRIPTION OF THE PREFERRED EMBODIMENTS

Figures 4, 5, 6:
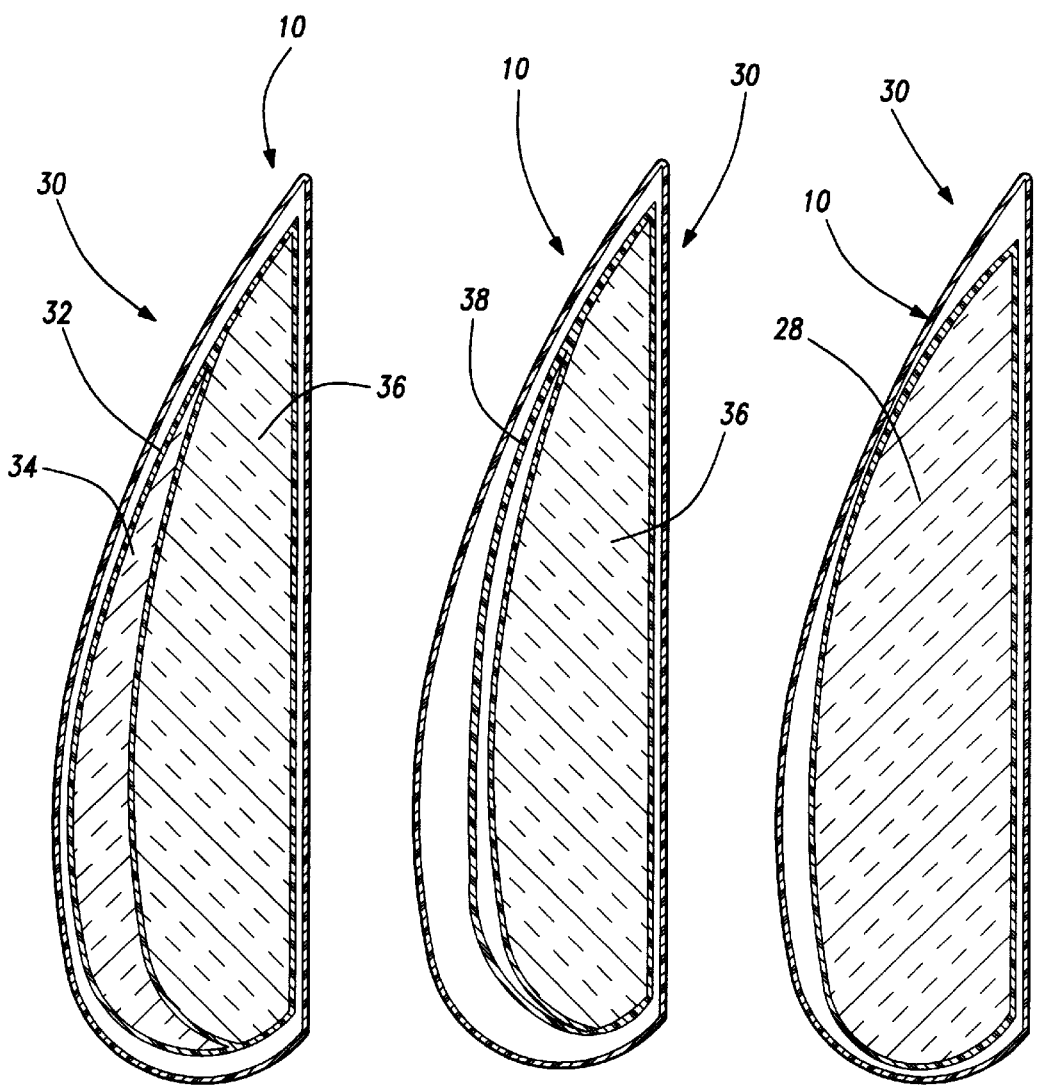
FIG. 4 is a side view of a bladder similar to FIG. 1 but with a double lumen breast prosthesis contained within the bladder, the outer and inner lumen both being filled with a liquid.
FIG. 5 is a side view similar to FIG. 4 with the liquid evacuated from the outer lumen.
FIG. 6 is a side view of a bladder similar to FIG. 1 with a conventional silicone breast prosthesis contained with the bladder.

Referring to FIGS. 1–3, the bladder 10 of a breast prosthesis implant of the present invention in FIG. 1 shows it expanded to its normal shape when the patient is in an upright position showing that it conforms to the natural tear-shaped sag of the female human breast. FIG. 2 shows a top view of the expanded position of the bladder of FIG. 1, and FIG. 3 shows a plan view of the bladder.

The bladder 10 is formed from a bio-compatible flexible thermoplastic polymer which can be molded in one piece or formed with a number of pieces such as the four piece structure indicated in FIG. 3 having a top strip 12, a middle strip 14, and a bottom strip 16 with an essentially planar back piece 18. The strips and back piece can be bonded together or otherwise joined as by stitching shown at 20 and 22 in FIG. 3 and at 24 in FIG. 2. The top, middle and bottom strips have overlapping portions shown at 26 to form the bottom seam 24. The bottom seam preferably overlaps no more than 5 mm. The bladder may have a preformed inlet cut into it as shown at 40 or one of the seams 20 and 22 may be left open to form an opening. Alternatively the surgeon may cut the opening in the bladder once it is in place in the chest cavity. It will be appreciated that the bladder 10 will be fairly flat before it is expanded by the insertion of a breast prosthesis.

The volume of the bladder 10 can vary widely depending on the size of the breast prosthesis, usually between 500 and 1000 ml and in any event they will be at least 25–30% larger than the intended prosthesis implant.

The material of the bladder is a bio-compatible flexible thermoplastic polymer and preferably Teflon® or polytetrafluoroethylene which can be purchased under the trade name Gore-Tex® in an expanded form having porosity between 15 and 100 microns and typically with an average porosity of 20–30 microns which has been found to be ideal to promote the growth of body tissue into the pores to form an artificial scar with minimal spherical capsular contracture so as to stent the surgical breast pocket open eliminating the contracture and preventing wrinkling or rippling of the skin. Obviously other non-degradable materials might be used such as a silicone, polyurethane, polyvinylalcohol, polyethylene, silastic or the like. The important aspect is that at least the outer surface of the material is microporous.

Another intrinsic or patent aspect of the bladder is the provision of means for at least temporary attachment or fixation of the bladder in the breast pocket to allow the ingrowth of body tissue which is usually accomplished in approximately three weeks after implant. One means is to provide the bladder with a peripheral attachment area 42 or spaced tabs so that the bladder can be located for example by stitches 90° apart. Another way to provide a temporary fixation is by using a double lumen breast prosthesis with an inner lumen being filled with a liquid to expand the prosthesis to a final desired extent. An outer lumen can then be filled with a liquid, after the prosthesis has been implanted, to expand the bladder to temporarily lodge or locate the bladder for tissue ingrowth. After three weeks, the liquid in the outer lumen can be withdrawn with a catheter to allow the natural shape of the inner lumen to remain. With the double lumen prosthesis, it can be made with a silicone rubber with a fairly strong inner lumen shell and a thin outer lumen shell. When the outer lumen is deflated, it will merely adhere to the inflated inner lumen. The inner lumen will be filled with a saline solution after implantation or whatever bio-compatible agent becomes available and is most satisfactory, i.e. having tactile properties similar to silicon gel, but perhaps with radiolucency and minimum biologic effects.

The breast prosthesis can be in the form of a standard silicone rubber containment sac filled with silicone gel where the bladder is preanchored by stitching. The advantage of the silicone rubber prosthesis is that they are commonly available in a wide variety of styles and sizes.

FIG. 6 shows the breast prosthesis 30, implant of the present invention with the bladder 10 containing a silicone rubber, silicone gel filled breast prosthesis 28.

FIG. 4 shows a double lumen breast prosthesis 32 implanted in the bladder 10 with the outer lumen 34 and the inner lumen 26 of the prosthesis filled with a liquid.

FIG. 5 is a showing similar to FIG. 4 with the liquid from the outer lumen 34 evacuated leaving perhaps a portion 38 of the outer lumen that does not completely adhere to the inner lumen.

The Surgical Method of implantation The surgical method for preforming a breast prosthesis implant is essentially the same for augmentation mammoplasty as it is for replacement mammoplasty and the claims of this application apply to both, but reference is primarily to augmentation mammoplasty.

In making the initial incision an areolar incision is preferred, but in either case other openings are satisfactory such as axillary or inframmary. A subcutaneous subglandular pocket can be dissected with blunt dissection followed by electrocautery dissection for hemostasis. Alternatively a submuscular pocket can also be formed in a similar manner. The pocket formed is then irrigated with an antibiotic solution such as a betadine solution and the pocket is reexamined to insure hemostasis.

The expanded polytetrafluoroethylene, e PTFE bladder is then introduced into the breast pocket. Optionally the bladder can be first placed into a 60 cc syringe with keflin solution and vacuum applied to try to infiltrate antibiotic into the membrane. Preferably the bladder is then introduced into the breast pocket from within a sterile sleeve to minimize contact and possible contamination with skin and breast tissue In a preferred form of the invention the bladder has a peripheral attachment area so that the bladder can be secured with a 4-O Gore-Tex suture thread to secure the bladder at four points: superior, inferior, medial and lateral poles.

Obviously dissolvable staples can also be used to secure the bladder. If the bladder does not have a previously made inlet, a 4–5 cm. incision is made in the bladder after implantation to provide an opened inlet.

A smooth wall silicone gel filled implant can then be inserted into the e PTFE bladder, and the opening can be closed with a 4-O Gore-Tex suture. With a medium frame and medium breast woman, the bladder can have a capacity of approximately 600 ml and a 260 cc smooth surface silicone gel implant can be used such as a McGhan style 40.

The breast wound can then be closed with a 4-0 vicyl sub-dermal and then 5-0 prolene on the skin in running horizontal mattress closure. New skin solution, steri strips, telfa pads and then a bra and ace bandage can then be applied.

In approximately 3 weeks the artificial scar should be well established, stenting the breast pocket open, allowing free movement of the breast prosthesis within the bladder.

An alternate method of temporarily securing the bladder in place during the tissue ingrowth period is by the use of a double lumen breast prosthesis. In this procedure the double lumen implant would be inserted through the opened inlet in the bladder after placement of the e PTFE bladder in the breast pocket. The inner lumen is then filled by a needle with a saline solution or other bio-compatible agent which has tactile properties similar to silicone gel to a volume which will give the final shape of the implant. The outer lumen is then filled with a saline solution to expand the bladder into a fixed position. After the tissue growth into the bladder pores has proceeded to create its artificial scar, usually about 3 weeks, an intravenous catheter is inserted through the breast tissue, in a tiny area of local anesthesia, until the outer lumen is punctured and the saline solution is expelled. This will complete the procedure leaving a soft, somewhat mobile implant within the synthetic scar.

It is apparent from the above description that the bladder 10 is preferably constructed of the same material throughout, i.e., preferably polytetrafluoroethylene with an average porosity of 20 to 30 microns throughout to promote tissue growth on the exterior surface and to discourage leakage through the bladder in the event the containment sac is ruptured.

Figure 7:
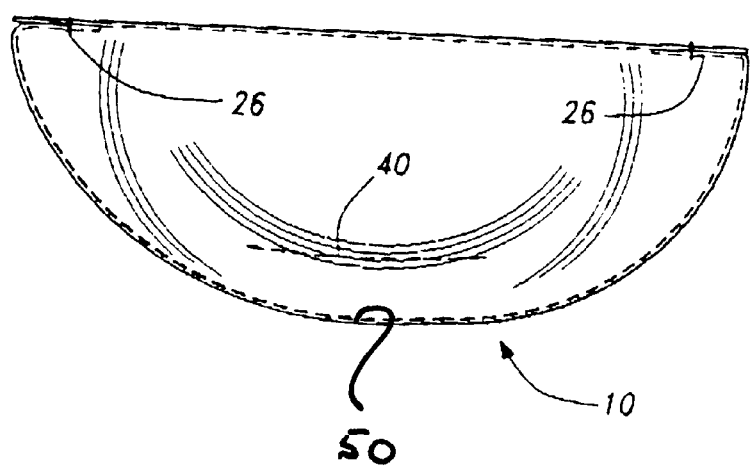
FIG. 7 is a view similar to FIG. 1 illustrating another preferred embodiment of the present invention.

As shown in FIG. 7 a coating 50 of silicone or other non-porous material can be provided on the inner surface of the bladder 10 to insure that tissue will not leak through to the interior of the bladder 10.

I claim:

1. A human body implant comprising, in combination:
   a bio-compatible flexible thermoplastic polymer bladder with at least its outer surface being microporous so that after implant in a subcutaneous pocket, body tissue will grow into the pores to form an artificial scar with minimal spherical capsular contracture;
   said bladder having an inlet; and
   apparatus including one of a body prosthesis and a physiological device introduced through said bladder inlet into said bladder after implant of said bladder, said inlet being subsequently sealed.

2. A breast prosthesis implant comprising, in combination:
   a bio-compatible flexible thermoplastic polymer bladder being microporous with a pore size between 15 and 100 microns so that after implant in a subcutaneous pocket, body tissue will grow into the pores to form an artificial scar with minimal spherical capsular contracture;
   said bladder being formed of the same material throughout and having a thin enough wall thickness so as to be non-palpable under subcutaneous tissue;
   said bladder further having an inlet and being expandable to a generally tear-drop shape; and
   a soft pliable breast prosthesis introduced into said bladder through said bladder inlet after implant of said bladder, said inlet being subsequently sealed and said prosthesis expanding said bladder to a desired shape.

3. The breast prosthesis implant according to claim 2 wherein at least the outer surface of said bladder has a pore size between 15 and 100 microns.

4. The breast prosthesis implant according to claim 2 wherein said bladder is formed of expanded polytetrafluoroethylene.

5. The breast prosthesis implant according to claim 2 wherein said bladder comprises a plurality of pieces which are joined together.

6. The breast prosthesis according to claim 5 wherein said pieces are stitched together.

7. The breast prosthesis implant according to claim 2 wherein said bladder has a wall thickness between 0.2 mm and 0.4 mm.

8. The breast prosthesis implant according to claim 2 wherein said breast prosthesis comprises an outer polymer shell filled with a liquid.

9. The breast prosthesis implant according to claim 8 wherein said outer shell is a silicone rubber filled with a silicone gel.

10. The breast prosthesis implant according to claim 8 wherein said outer shell is filled with a saline solution.

11. The breast prosthesis implant according to claim 2 wherein said bladder has a peripheral attachment area.

12. The breast prosthesis implant according to claim 8 wherein said breast prosthesis is constructed with a double lumen, having an outer polymer lumen shell and an inner polymer lumen shell.

13. The breast prosthesis implant according to claim 12 wherein at least the inner lumen shell is filled with a liquid.

14. The breast prosthesis according to claim 13 wherein said outer lumen shell is filled with a liquid.

15. The implant as defined in claim 1 and in which said bladder has an inner surface, said inner surface being coated with a non-porous material.

16. A method of performing a breast prosthesis implant comprising the following steps:

A) making an incision and creating a subglandular or submuscular breast pocket by dissection followed by hemostasis;

B) irrigating said breast pocket with an antibiotic solution;

C) providing a bio-compatible thermoplastic polymer bladder with at least its outer surface being microporous, the bladder having a wall thickness between 0.2 mm and 1.2 mm and being expandable to a tear drop shape;

D) introducing the bladder into the breast pocket created in step A);

E) securing said bladder in said breast pocket;

F) providing a soft pliable smooth surface breast prosthesis;

G) opening an inlet in the bladder;

H) introducing the breast prosthesis into the bladder through said opened inlet, and expanding the bladder to a desired shape with the prosthesis remaining at least partially mobile within said bladder;

I) closing the inlet in the bladder, and

J) allowing host body tissue to grow into said pores forming an artificial scar in a manner which prevents or minimizes spherical capsular contracture.

17. The method according to claim 16 wherein in step C) said bladder comprises a plurality of pieces which are stitched together.

18. The method according to claim 17 wherein said bladder as provided in step C) has an inlet which is opened in steps G) and is closed in step I).

19. The method according to claim 18 wherein a seam between two pieces is left unstitched to provide said inlet in said bladder.

20. The method according to claim 6 wherein the inlet is cut and opened in the bladder in step G) after the bladder has been introduced into the breast pocket in step D).

21. The method according to claim 16 wherein the bladder provided in step C) has a peripherally located attachment area and the bladder is secured in step E) by stitching through the attachment area.

22. The method according to claim 16 wherein the breast prosthesis provided in step F) has an outer shell of silicone rubber filled with silicone gel.

23. The method according to claim 16 wherein in step F) a double lumen breast prosthesis is provided, and after it has been introduced into the bladder in step H), an inner lumen of the prosthesis is filled by a catheter with a bio-compatible liquid, and an outer lumen of the prosthesis is filled by a catheter with a bio-compatible liquid, the filling of the outer lumen expanding the bladder to temporarily secure the bladder in the breast pocket in step E) with final securing being obtained in step J) by the formation of the artificial scar, after which the bio-compatible liquid is removed from the outer lumen by a catheter, and the bladder assumes a desired final shape with the breast prosthesis being at least partially mobile within the bladder so as to not cause wrinkling of the skin.

* * * * *